US00PP32311P2

(12) United States Plant Patent
Bergman

(10) Patent No.: US PP32,311 P2
(45) Date of Patent: Oct. 13, 2020

(54) ***LANTANA* PLANT NAMED 'LANZ0027'**

(50) Latin Name: ***Lantana camara* L.**
Varietal Denomination: LANZ0027

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,569

(22) Filed: May 1, 2019

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./227
CPC ..... A01H 5/02; A01H 5/00; A01H 6/86
See application file for complete search history.

(56) References Cited

PUBLICATIONS

Issuu Syngenta Flowers Annuals & Perennials 2020 UK, retrieved on Jan. 22, 2020, retrieved from the Internet at https://issuu.com/floriproservices/docs/a_p_2020_150dpi_uk, cover page and p. 231. (Year: 2020).*

Syngenta Novelty Presentation E2 varieties 2018-2019 Annual Cuttings, retrieved on Jan. 22, 2020, retrieved from the Internet at https://www.seedstar.sk/assets/img/FPS-varieties-annual-cuttings-season-2018-2019.pdf, cover page, pp. 2 and 87. (Year: 2019).*

* cited by examiner

*Primary Examiner* — June Hwu
(74) *Attorney, Agent, or Firm* — Dale Skalla

(57) ABSTRACT

A new *Lantana* plant named 'LANZ0023' having white mature flowers, excellent flower production, large plant size and uniform densely mounding plant habit with medium green foliage.

1 Drawing Sheet

Latin name of the genus and species of the plant claimed: *Lantana camara* L.

Varietal denomination: 'LANZ0027'.

BACKGROUND OF THE NEW PLANT

The present invention comprises a new *Lantana*, botanically known as *Lantana camara* L., and hereinafter referred to by the variety name 'LANZ0027'.

'LANZ0027' is a product of a planned breeding program. The new cultivar 'LANZ0027' has white mature flowers, excellent flower production, large plant size and uniform densely mounding plant habit with medium green foliage.

'LANZ0027' originates from an open hybridization in an outdoor field in August, 2014 in Gilroy, Calif. The female parent was identified as 'F0005-3' a proprietary breeding line having white flowers and a smaller plant size. The male parent of 'LANZ0027' is unknown.

The seed was sown in March 2015 in a greenhouse in Gilroy, Calif. and 'LANZ0027' was selected as one flowering plant within the progeny of the stated cross in June 2015.

The first act of asexual reproduction of 'LANZ0027' was accomplished when vegetative stem cuttings were propagated from the initial selection in August 2015, in a greenhouse in Gilroy, Calif.

BRIEF SUMMARY OF INVENTION

Horticultural examination of plants grown from cuttings of the plant initiated in August, 2015, in Gilroy, Calif., and continuing thereafter, has demonstrated that the combination of characteristics as herein disclosed for 'LANZ0027' are firmly fixed and are retained through successive generations of asexual reproduction.

'LANZ0027' has not been observed under all possible environmental conditions. The phenotype may vary significantly with variations in environment such as temperature, light intensity, and day length.

A Plant Breeder's Right for this cultivar has not yet been applied for. 'LANZ0027' has not been made publicly available prior to the effective filing date of this application, notwithstanding any disclosure that may have been made less than one year prior to the effective filing date of this application by the inventor or another who obtained 'LANZ0027' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

Figure 1:
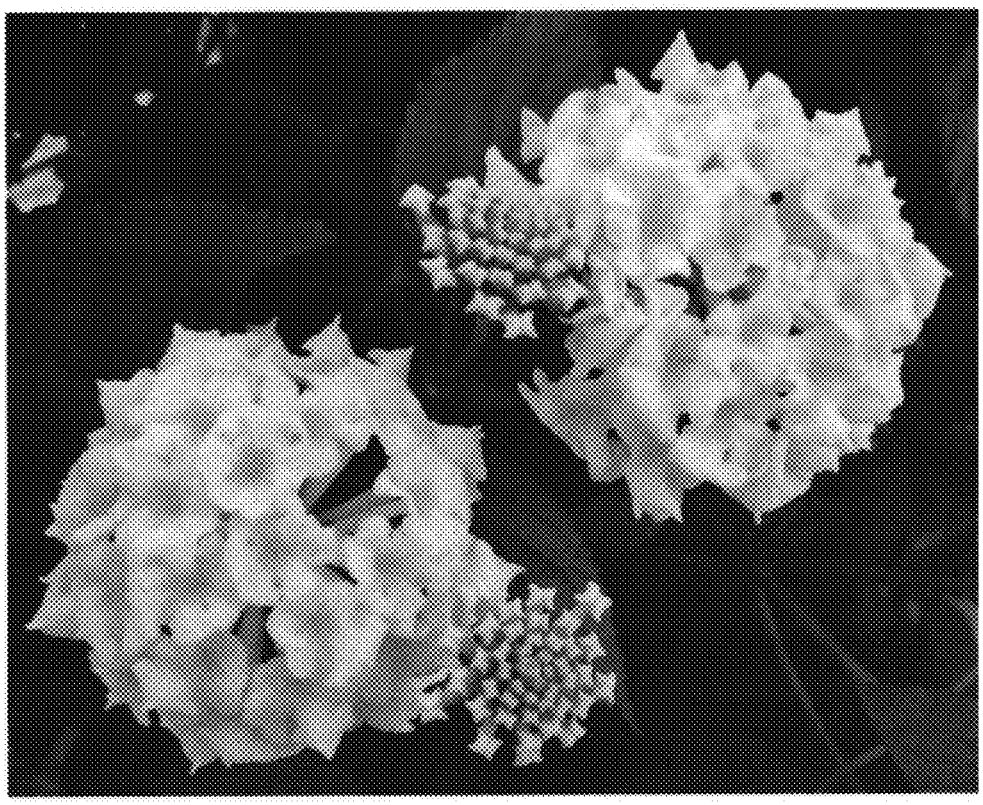
Figure 2:
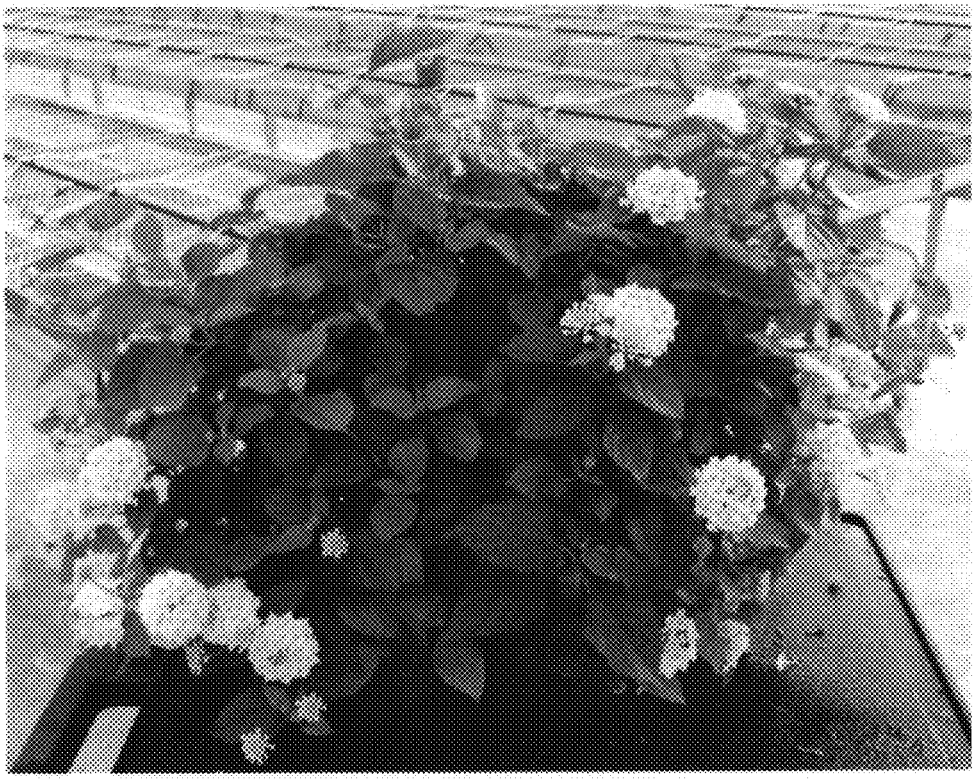

The accompanying photographic drawings show typical flower and foliage characteristics of 'LANZ0027' with colors being as true as possible with an illustration of this type. The photographic drawings show in FIG. 1 a close view of an inflorescence, and in FIG. 2 a whole flowering plant.

DETAILED BOTANICAL DESCRIPTION

The plant descriptions and measurements were taken in Gilroy, Calif. in April 2019. The plants were approximately 8 months old and were growing in gallon pots in a greenhouse.

The aforementioned photographs show those same plants as used for the description were taken in Gilroy, Calif. in April 2019 and show 8 month old plants from an indoor trial.

Color references are made to The Royal Horticultural Society Colour Chart (R.H.S.) 2001.

TABLE 1

DIFFERENCES BETWEEN THE NEW VARIETY 'LANZ0027' AND A MOST SIMILAR VARIETY

| | 'LANZ0027' | 'Ban Whit', (U.S. Plant Pat. No. 21,590) |
|---|---|---|
| Mature flower color: | White | White |
| Plant height: | Taller | Shorter |
| Plant width: | Wider | Smaller |
| Seed set: | More | Less |

Plant:

*Form, growth and habit.*—Semi-woody, grown as an annual or perennial; large and dense mounding habit; very well branched.

*Plant height.*—29 cm.

*Plant height* (*inflorescence included*).—31 cm.

*Plant width.*—66 cm.

Foliage:

*Type.*—Opposite.

*Fragrance.*—Strongly scented.

*Immature, leaf color, upper surface.*—Closest to RHS 137B.

*Lower surface.*—Closest to RHS 137C.

*Mature, leaf color, upper surface.*—RHS 139A.

*Lower surface.*—Closest to RHS 137B.

*Length.*—7.0-8.4 cm.

*Width.*—4.8-5.4 cm.

*Shape.*—Ovate.

*Base shape.*—Rounded.

*Apex shape.*—Acute.

*Margin.*—Dentate.

*Texture, upper.*—Strigose.

*Texture, lower surface.*—Strigose.

*Pattern of veining.*—Pinnate.

*Petioles color.*—RHS 137C.

*Petioles length.*—1.8-2.1 cm.

*Diameter of petiole.*—0.20 cm.

*Texture* (*upper and lower surface*).—Very short hairs.

Stem:

*Color of stem.*—RHS 146B.

*Length of stem.*—22-27 cm.

*Diameter.*—0.2-0.3 cm.

*Length of internodes.*—2.5-5.0 cm.

*Texture.*—Hirsute.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 50-54.

*Quantity of inflorescences per plant.*—About 42.

*Lastingness of individual blooms on the plant.*—About 3 weeks (depending on temperatures).

*Fragrance.*—Slightly spicy.

*Umbel horizontal diameter.*—4.8-5.2 cm.

*Umbel vertical height.*—2.6 cm.

*Peduncle color.*—RHS 146B.

*Length of peduncle.*—4.3-5.2 cm.

*Peduncle diameter.*—0.15-0.2 cm.

*Texture.*—Scabrous.

Flower:

*Floret form.*—Corolla salver-shaped to shallow cup-shaped, with a relatively long tube at the base; each flower subtended by a single bract.

*Average number of florets per inflorescence.*—37-40.

*Length of floret.*—2.2-2.4 cm.

*Width of floret.*—1.1 cm.

*Depth of floret.*—1.5 cm.

*Number of corolla lobes per floret.*—4 lobes.

*Young floret, color upper surface.*—RHS 1D with RHS 12A throat.

*Young floret, color lower surface.*—RHS 4D.

*Mid age floret, color upper surface.*—RHS 155A with RHS 5A throat.

*Mid age floret, color lower surface.*—RHS 155A.

*Mature florets, color upper surface.*—RHS 155D.

*Mature floret, color lower surface.*—RHS 155D.

*Apex shape.*—Rounded.

*Degree of lobation.*—Moderate.

*Margin.*—Entire.

*Base.*—Fused.

*Texture, upper surface.*—Smooth.

*Lower surface.*—Smooth.

*Tube, color outer surface.*—RHS 155D.

*Tube, color inner surface.*—RHS 155D.

*Tube, length.*—1.4-1.5 cm.

*Tube, diameter* (*at opening*).—0.2 cm.

*Tube, texture outer surface.*—Very small hairs.

*Inner surface.*—Smooth.

Bud (just before opening):

*Color.*—RHS 1D.

*Length.*—1.3 cm.

*Width.*—0.4 cm at the apex.

*Shape.*—Tubular with a flared apex.

Bract:

*Color, upper and lower surfaces.*—Closest to RHS 137C.

*Length.*—0.6-0.8 cm.

*Diameter.*—0.2 cm.

*Texture, upper surface.*—Small hairs.

*Lower surface.*—Small hairs.

Calyx:

*Number of sepals.*—5, fused sepals forming a short tube around the base of the floret.

*Color of sepals, upper and lower surfaces.*—RHS 145A.

*Length of sepals.*—0.2 cm.

*Width of sepals.*—0.15 cm.

*Apex shape.*—Obtuse.

*Apex margins.*—Entire.

*Texture, outer surface.*—Small hairs.

*Inner surface.*—Smooth.

Reproductive organs:

Gynoecium:

*Pistil quantity.*—One.

*Length.*—0.4 cm.

*Style color.*—RHS 150D.

*Style length.*—0.3 cm.

*Stigma color.*—RHS 143C.

*Ovary color.*—RHS 143C.

*Ovary length.*—0.1 cm.

*Ovary diameter.*—0.05 cm.

Androecium:

*Stamen quantity.*—4.

*Color of filaments.*—RHS 159D.

*Length filaments.*—0.05 cm.

*Anther color.*—RHS 4C.

*Length of anthers.*—0.1 cm.

*Color of pollen.*—RHS 4D.

*Pollen amount.*—Scant.

*Fertility/seed set.*—Moderate.

*Fruit.*—Round drupe.

*Immature fruit color.*—RHS 146B.

*Mature fruit color.*—RHS 202A.

*Mature fruit size.*—0.5-0.6 cm in diameter.

*Texture of mature fruit.*—Fleshy.

*Disease/pest resistance.*—Has not been observed to date.

*Plant hardiness zone.*—Hardy to Zone 9B.

*Heat/cold resistance.*—Very heat tolerant.

What is claimed is:

1. A new and distinct variety of *Lantana* plant named 'LANZ0027' substantially as illustrated and described herein.

* * * * *